United States Patent [19]

Hofstead et al.

[11] Patent Number: 5,001,112
[45] Date of Patent: Mar. 19, 1991

[54] ANTITUMOR ANTIBIOTIC KEDARCIDIN

[75] Inventors: Sandra J. Hofstead, Middletown; James A. Matson, Cheshire; Kin S. Lam, Cheshire; Salvatore Forenza, Cheshire; James A. Bush, Cheshire, all of Conn.; Koji Tomita, Tokyo, Japan

[73] Assignee: Bristol-Myers Company, New York, N.Y.

[21] Appl. No.: 323,001

[22] Filed: Mar. 17, 1989

Related U.S. Application Data

[63] Continuation-in-part of Ser. No. 180,519, Apr. 12, 1988, abandoned.

[51] Int. Cl.$^5$ .............................................. A61K 37/02
[52] U.S. Cl. ...................................... 514/12; 530/350; 530/324; 435/71.3; 514/6
[58] Field of Search ............... 530/324, 350, 317, 400; 435/68, 71.3; 514/12, 6

[56] References Cited

U.S. PATENT DOCUMENTS

| | | | |
|---|---|---|---|
| 3,992,524 | 11/1976 | Umezawa et al. | 424/89 |
| 4,156,719 | 5/1979 | Sezaki et al. | 424/89 |
| 4,182,752 | 1/1980 | Maeda et al. | 435/68 |
| 4,328,211 | 5/1982 | Sugawara et al. | 435/169 |
| 4,507,282 | 3/1985 | Udaka et al. | 424/89 |
| 4,746,675 | 5/1988 | Makino et al. | 514/423 |

OTHER PUBLICATIONS

Kuromizu, K. et al., Re-Examination of the Primary Structure of an Antitumor Protein, Neocarzinostatin, Arch. Biochem. Biophy., 1986, 246:199-205.
Gibson, B. W. et al., A Revised Primary Structure for Neocarzinostatin Based on Fast Atom Bombardment and Gas-Chromatographic-Mass Spectrometry, J. Biol. Chem., 1984, 259:10801-10806.
Samy, T. S. A. et al., Primary Structure of Macromomycin, an Antitumor Antibiotic Protein, J. Biol. Chem., 1983, 258:183-191.
Khokhlov, A. S. et al., Chemical Studies on Actinoxanthin, J. Antibiot., 1976, 29:1026-1034.
Miyaki et al., J. Antibiot., 34(6), 665-74, Chem. Abs. 95(9), 78406t, (1981).
Miyaki et al., J. Antibiot., 34(6), 658-64, (1981), Chem. Abs. 95(9), 78405s.
Miyaki et al., Chem. Abs. 94(25), 207415n (1981).
Tomita et al., J. of Antibotics, 1978, pp. 497-510.

Primary Examiner—Johnnie R. Brown
Assistant Examiner—T. Wessendorf
Attorney, Agent, or Firm—Mollie M. Yang

[57] ABSTRACT

Kedarcidin is a protein antitumor antibiotic produced by Streptoalloteichus sp. nov. strain L585-6, ATCC 53650. The antibiotic comprises a non-protein chromophore and a single chain polypeptide having 114 amino acid residues.

2 Claims, 1 Drawing Sheet

ULTRAVIOLET SPECTRUM OF ANTIBIOTIC KEDARCIDIN

ULTRAVIOLET SPECTRUM OF ANTIBIOTIC KEDARCIDIN

ANTITUMOR ANTIBIOTIC KEDARCIDIN

This application is a continuation-in-part of U.S. Ser. No. 180,519 filed on Apr. 12, 1988, now abandoned.

BACKGROUND OF THE INVENTION

The present invention relates to antitumor antibiotic herein designated as kedarcidin, to its production by Streptoalloteichus sp. nov. Strain L585-6, to pharmaceutical compositions containing the antibiotic and to method of inhibiting tumor growth by said antibiotic. The invention also relates to the kedarcidin-producing microorganism Streptoalloteichus sp. nov. Strain L585-6, ATCC 53650.

SUMMARY OF THE INVENTION

The present invention provides antitumor antibiotic kedarcidin which is characterized as follows:
 (a) appearance: buff-colored solid;
 (b) molecular weight: 12,400 daltons by SDS-polyacrylamide gel electrophoresis method, 17,000 by gel filtration/HPLC method;
 (c) UV spectrum: substantially as shown in FIG. 1;
 (d) isoelectric point: 3.65; and
 (e) comprises a polypeptide having an amino acid sequence as follows:
 X-ala-ala-val-ser-val-ser-pro-ala-thr-gly-leu-ala-asp-gly-ala-thr-val-thr-val-ser-ala-ser-gly-phe-ala-thr-ser-thr-ser-ala-thr-ala-leu-gln-cys-ala-ile-leu-ala-asp-gly-arg-gly-ala-cys-asn-val-ala-glu-phe-his-asp-phe-ser-leu-gly-gly-glu-gly-thr-val-ser-val-val-arg-arg-ser-phe-thr-gly-tyr-val-met-pro-asp-gly-pro-glu-val-gly-ala-val-asp-cys-asp-thr-ala-pro-gly-gly-cys-gln-ile-val-val-gly-gly-asn-thr-gly-glu-tyr-gly-asn-ala-ala-ile-ser-phe-gly-OH;
 wherein
X is selected from the group consisting of H-ala-ser, H-ser and H.

The physico-chemical characteristics given above distinguish the antibiotic of the present invention from other known peptide antibiotics having antitumor activity such as neocarzinostatin, macromomycin, largomycin, actinoxanthin and AN-7D.

The present invention provides further a process for the production of antibiotic kedarcidin which comprises cultivating a kedarcidin-producing strain of Streptoallolelohus in a medium containing assimilable sources of carbon and nitrogen under submerged aerobic conditions, and recovering said protein from the fermentation broth.

A further aspect of the invention provides a kedarcidin-producing strain of Streptoalloteichus sp. nov. strain L585-6. ATCC 53650.

Yet another aspect of the invention provides a pharmaceutical composition comprising a tumor-inhibiting amount of antibiotic kedarcidin and a pharmaceutically acceptable carrier.

A further aspect of the invention provides a method for inhibiting tumor growth in a mammalian host which comprises administering to said tumor-bearing host a tumor-inhibiting amount of antibiotic kedarcidin.

DETAILED DESCRIPTION OF THE INVENTION

Figure 1:
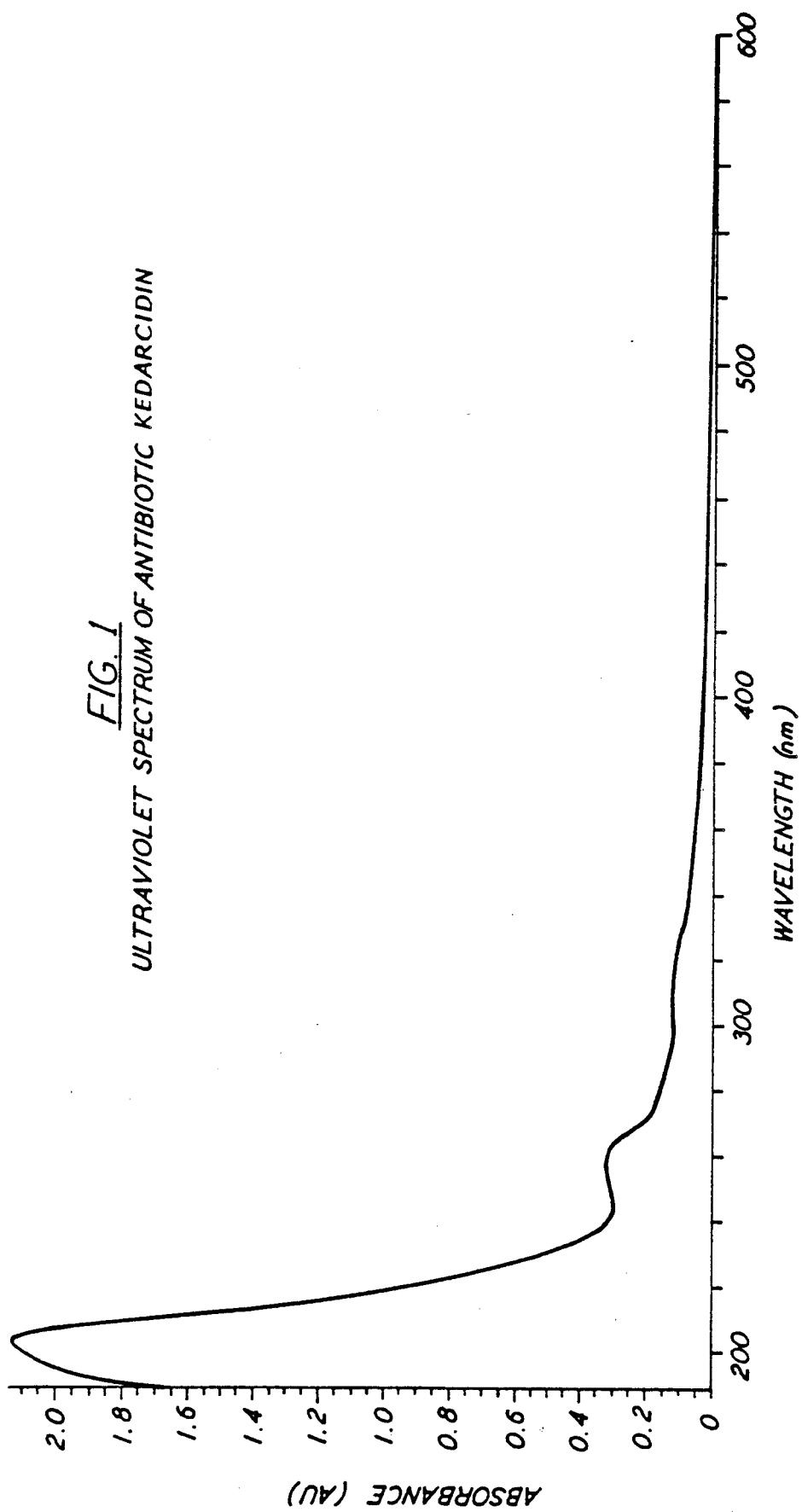
FIG. 1 shows a UV spectrum of antibiotic kedarcidin.

As used herein, the following abbreviations are used to represent the amino acids:
asx: aspartic acid asparagine
thr: threonine
scr: serine
glx: glutamic acid + glutamine
asp: aspartic acid
asn: asparagine
glu: glutamic acid
gln: glutamine
pro: proline
gly: glycine
ala: alanine
val: valine
met: methionine
ile: isoleucine
leu: leucine
tyr: tyrosine
phe: phenylalanine
his: histidine
lys: lysine
arg: arginine
cys: cysteine
trp: tryptophan

Producing Organism

Strain L585-6 was isolated from a soil sample collected in Maharastra State, India. Characteristics of Strain L585-6 are described in detail herein below:

Morphology

Strain L585-6 is a gram-positive, filamentous organism that forms substrate and aerial mycelia. The substrate mycelium penetrates the agar and is not fragmented. Globose dense aggregates of hyphae, 5 to 25 μm in diameter, along with coalesced vegetative hyphae, are observed. The aerial mycelium is well branched and develops straight slewing or spiral long hyphae, in which spores are formed in continuous or discontinuous chain. Dense tufts of branched short spore chains are formed predominantly in ISP medium No. 5. Both types of spores are oval to short-cylindrical (0.4 to 0.6 by 1.0 to 2.0 μm), non-motile, and have smooth surface.

Colorless balloon-like bodies (5 to 20 μm in diameter) are observed singularly or in mass on the aerial mycelium after incubation for 5 to 10 days. After incubation for three weeks or more, these balloon-like bodies develop into yellowish-brown sclerotic granules (40 to 100 μm in diameter) which are covered with further elongated aerial hyphae.

Cultural characteristics

The growth is generally moderate, but is very poor on Czapek's sucrose-nitrate agar, oatmeal agar and starch-mineral salts agar. The aerial mycelium is formed on the tyrosine agar and glycerol-asparagine agar, but not on ISP media nos. 2, 3, 4 and 6, and Bennett's agar. The color of the aerial mycelium is yellowish white. Blackish melanoid pigments are formed in ISP media nos. 6 and 7. The other distinct pigments are not formed. The cultural characteristics of Strain L585-6 are shown in Table I.

TABLE I

Cultural characteristics of Strain L585-6

| Medium | Characteristics[1] |
|---|---|
| Sucrose-nitrate agar (Czapek-Dox agar) | [2]G: none or scant<br>A: none<br>S: colorless<br>D: none |
| Tryptone-yeast extract broth (ISP No. 1) | G: moderate; not turbid, floccose<br>A: none<br>S: colorless<br>D: deep yellowish-brown (75)[3] |
| Yeast extract-malt extract agar (ISP No. 2) | G: moderate<br>A: none<br>S: dark yellowish-brown (78)<br>D: deep yellowish-brown (75) |
| Oat meal agar (ISP No. 3) | G: scant<br>A: none or scant; white when present<br>S: colorless<br>D: none |
| Inorganic salts-starch agar (ISP No. 4) | G: scant<br>A: none or scant; white when present<br>S: colorless<br>D: none |
| Glycerol-asparagine agar (ISP No. 5) | G: moderate<br>A: moderate; yellowish-white (92)<br>S: colorless<br>D: none |
| Peptone-yeast extract-iron agar (ISP No. 6) | G: moderate<br>A: none<br>S: light grayish-yellowish brown (79)<br>D: brownish black (65) |
| Tyrosine agar (ISP No. 7) | G: moderate<br>A: abundant; yellowish-white (92)<br>S: black<br>D: black |
| Glucose-asparagine agar | G: poor<br>A: none<br>S: dark orange-yellow (72)<br>D: none |
| Bennett's agar | G: moderate<br>A: none or scant; white when present<br>S: dark grayish-yellowish brown (81)<br>D: moderate yellowish-brown (77) |

[1]observation after incubation at 28° C. for 3 weeks.
[2]G = growth; A = aerial mycelium; S = substrate mycelium; D = diffusible pigment.
[3]color and number in parenthesis follows ISCC-NBS designation.

Physiological characteristics

Optimal growth is observed at 30° to 35° C. The temperature range for growth is 18° C. to 39° C. No growth occurs at 15° C. and 41° C.; no growth occurs on media supplemented with more than 5% NaCl. Gelatin is liquefied but starch is not hydrolyzed. Among 25 sugars tested, only D-ribose and D-glucose are utilized for growth. The physiological characteristics and carbohydrate utilization are shown in Tables II and III.

TABLE II

Physiological characteristics of strain L585-6

| Hydrolysis of | | Utilization of [*2] | |
|---|---|---|---|
| Gelatin | + | L-Rhamnose | − |
| Starch | | D-Glucose | + |
| Soluble starch | − | D-Galactose | − |
| Potato starch | − | D-Fructose | − |
| Milk coagulation | + | D-Mannose | − |
| peptonization | + | L-Sorbose | − |
| Production of | | Sucrose | − |
| Nitrate-reductase | − or<br>+(w)[*1] | Lactose | − |
| | | Cellobiose | − |

TABLE II-continued

Physiological characteristics of strain L585-6

| | | Utilization of [*2] | |
|---|---|---|---|
| Tyrosinase | + | Melibiose | − |
| Tolerance to | | Trehalose | − |
| Lysozyme, 0.01% (w/v) | + | Raffinose | − |
| NaCl, 1%–4% (w/v) | + | D-Melezitose | − |
| NaCl, 5% | − | Soluble starch | − |
| pH, 5.0–11.0 | + | Cellulose | − |
| pH, 4.5 and 12 | − | Dulcitol | − |
| Temperature | | Inositol | − |
| Growth range | 18° C.–39° C. | D-Mannitol | − |
| No growth | 15° C. & 41° C. | D-Sorbitol | − |
| Optimal growth | 30° C.–35° C. | Salicin | − |
| | | Glycerol | − |
| | | D-Arabinose | − |
| | | L-Arabinose | − |
| | | D-Xylose | − |
| | | D-Ribose | + |

[*1]Negative in Czapek's sucrose-nitrate broth, and positive in peptone-nitrate broth.
[*2]Basal medium: Pridham-Gottlieb's medium (= ISP No. 9 medium)

TABLE III

Additional physiological characteristics* of strain L585-6

| Hydrolysis of | | Acid from | |
|---|---|---|---|
| Adenine | − | Glycerol | − |
| Casein | + | D-Arabinose | − |
| Esculine | + | L-Arabinose | − |
| Hippuric acid | + | D-Xylose | − |
| Hypoxanthine | − | L-Rhamnose | − |
| Tyrosine | + | D-Glucose | + |
| Urea | − | D-Mannose | − |
| Xanthine | − | Lactose | − |
| | | Cellobiose | − |
| Survival at 50° C., 8 hr | − | Melibiose | − |
| | | Trehalose | − |
| Utilization of | | Raffinose | − |
| Benzoate | − | D-Melezitose | − |
| Citrate | − | Inositol | − |
| Mucate | − | D-Mannitol | − |
| Succinate | + | D-Sorbitol | − |
| Tartrate | − | Erythritol | − |
| | | Adonitol | − |
| | | Methyl α-glucoside | − |

*The tests described by Gordon et al. J. Gen. Microb., 1978, 109: 69–78.

Cell Wall Chemistry

The cell wall content of strain L585-6 was examined according to the methods described by Becker et al. in Appl. Microbiol. 13: 236–243 (1965), by Yamaguchi in J. Bacteriol. 89: 444–453 (1965) and by Lechevalier and Lechevalier in Biology of the Actinomycetes and Related Organisms 11: 78–92 (1976). The cell wall peptidoglycan contains meso-diaminopimelic acid. Whole cell-sugars include galactose, glucose and ribose. Hence, the cell wall type belongs to Type IIIC Phospholipids are Type P-II containing phosphatidylethanolamine, phosphatidylglycerol and phosphatidylinositol. The major menaquinones are MK-9($H_4$) and MK-9($H_6$) Glycolate test is negative.

Taxonomy

Among the genera of Actinomycetales with long chains of spores, Pseudonocardia, Saccharopolyspora, Actinopolyspora, Streptomyces. Actinomadura. Glycomyces, Nocardiopsis and Amycolata are clearly differentiated from strain L585-6 in the cell chemistry comprising the cell wall type, cell sugar pattern, phospholipid and menaquinone. Kibdelosporangium (by Shearer et al., Int. J. Syst. Bacteriol. 36:47–54, 1986), Kitasatosporia (by Takahashi et al. J. Gen. Appl. Microbiol. 30: 377–387, 1984) and Amycolatopsis (by Lechevalier et al. Int. J. Syst. Bacteriol. 36: 29–37, 1986) are related to strain L585-6 in the composition of phospholipid and menaquinone, but Kibdelosporangium and Amycolatopsis differ from the strain in the presence of arabinose in cell wall sugar, and Kitasatosporia in the presence of both LL-and meso-diaminopimelic acid in the cell wall. In addition, Kibdelosporangium bears hypha-enveloping sporangium-like body with true membrane and Kitasatosporia forms submerged spores. These unique structures are not observed in strain L585-6. Chemotaxonomically, Streptoalloteichus (by Tomita et al. Int. J. Syst. Bacteriol. 37:211–213, 1987), Actinosynnema (by Hasegawa et al. Int. J. Syst. Bacteriol. 28: 304–310, 1978) and Saccharothrix (by Labeda et al. Int. J. Syst. Bacteriol. 34: 426–431, 1984) are most related to strain L585-6. Actinosynnema forms aerial spore chain from the tip of a synnema. Saccharothrix forms chains of fragmented coccoid elements in both vegetative and aerial mycelia and does not form cluster of branched short spore chain or sclerotic granule. The morphology of the chains of coccoid elements in *Saccharothrix australiensis* and *S. aerocolonigenes* (by Labeda. Int. J. Syst. Bacteriol. 36: 109–110, 1986) are related to those of Nocardiopsis but unrelated to any species of Streptomyces. Hence, strain L585-6 is placed in neither Actinosynnema nor Saccharothrix.

*Streptoalloteichus hindustanus* bears long spiral spore chain of arthrospores, branched short spore chain and sclerotic granule in the aerial mycelium and dense globose body of hyphae as well as small sporangium-like body enveloping one to four spores with flagellum in the vegetative mycelium. Strain L585-6 forms all of the small sporangium-like vesicles. Like Streptoalloteichus, strain L585-6 forms balloon-like body, which develops into sclerotic granule. This structure has been observed in many species of Streptomyces such as *S. kanamyceticus* (by Shirling et al. Int. J. Syst. Bacteriol. 22: 265–394, 1972) and *S. roseiscleroticus* (*Chainia rubra*) (by Shirling et al. Int. J. Syst. Bacterial. 22: 26514 394, 1972).

Based on the above-mentioned comparative considerations, strain L585-6 is classified into the genus Streptoalloteichus. Strain L585-6 differs from *Streptoalloteichus hindustanus* in the absence of ability to form aerial mycelium in ISP media Nos. 2, 3, and 4 and Bennett3 s agar, the formation of melanin, the absence of starch hydrolysis, the absence of growth at 41° C. and the ability to utilize only D-ribose and D-glucose among the 25 sugars tested. Thus strain L585-6 is considered to be a new species of the genus Streptoalloteichus.

A biologically pure culture of Strain L585-6, determined to be a new species of the genus Streptoalloteichus, has been deposited in the American Type Culture Collection (Rockville, Md.) and added to its permanent collection of microorganisms as ATCC 53650.

Antibiotic Production

The antitumor antibiotic of the present invention is produced by cultivating strain L585-6 or a mutant thereof under submerged conditions in an aqueous nutrient medium. The producing organism is grown in a nutrient medium containing an assimilable carbon source, for example an assimilable carbohydrate. Example of suitable carbon sources include cerelose and glycerol. The nutrient medium should also contain an assimilable nitrogen source such as fish meal, yeast extract or ammonium salts. Inorganic salts such as sodium chloride, potassium chloride, magnesium sulfate, calcium carbonate, phosphates, etc. are added if necessary. Trace elements such as copper, manganese, iron, zinc, etc. are added to the medium if desired, or they may be present as impurities of other constituents of the media. The incubation temperature may be any temperature at which the producing strain is able to grow e.g. 18° C. to 39° C., but it is preferable to conduct the fermentation at 25° C.-35° C., most preferably at 27° C.-32° C. A neutral pH is preferably employed in the medium and production of the antibiotic is generally carried out for a period of about 4 to 8 days. Ordinarily, optimum production is achieved in about 5–6 days. For preparation of relatively small amounts of the antibiotic, shake flask and surface culture can be employed, but for the preparation of larger amounts, submerged aerobic culture in sterile tanks is preferred. When tank fermentation is to be carried out, it is desirable to produce a vegetative inoculum in a nutrient broth by inoculating the broth culture with spores from the organism and when a young active vegetative inoculum has been obtained, transferring the inoculum aseptically to the fermentation tank medium. Further agitation may be provided by a mechanical impeller. Antifoam agents such as lard oil or silicone oil may also be added if needed.

Production of antibiotic kedarcidin in the fermentation medium can be readily followed during the course of fermentation by antimicrobial assays using *Bacillus subtilis* as the test organism or by cell cytotoxicity assay using murine (B16-F10) or human (e.g. HCT-116, KB) tumor cell lines.

It is to be understood that the present invention is not limited to the use of the particular preferred strain L585-6 described above or to organisms fully answering the above description. It is especially intended to include other kedarcidin-producing strains or mutants of the said organism which can be produced by conventional means such as x-rays radiation, ultraviolet radiation, treatment with nitrogen mustards, phage exposure and the like.

Isolation and Purification of Antibiotic

The antitumor protein of the present invention may be isolated from the fermentation broth using conventional protein separation methodologies such as dialysis, ultrafiltration, gel filtration, isoelectric precipitation, salting out, electrophoresis, ion-exchange chromatography, and affinity chromatography. A combination of these techniques in sequence is generally used to purify the protein to apparent homogeneity. The isolation and purification process may be monitored and guided by microbiological assays such as *B. subtilis*, in vitro cytotoxicity assays against murine or human cancer cell lines, in vivo antitumor assays, or by physical methods such as UV or HPLC techniques. Scheme I depicts a typical isolation purification sequence. This particular sequence is for illustrative purpose only and it will be appreciated by those skilled in the art that different sequences using other methods may also be used so long as the protein is obtained in high purity and retains its biological activities.

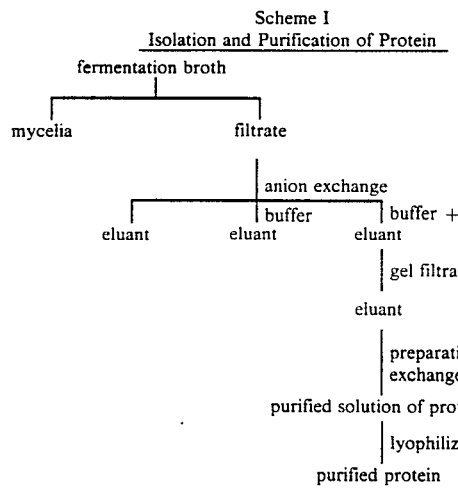

Scheme I
Isolation and Purification of Protein

To elaborate on Scheme I, insoluble mass of whole fermentation broth is removed using a conventional method such as centrifugation or filtration. If the broth is to be filtered a filter aid such as Dicalite may be advantageously used. The filtrate is then subjected to anionic-exchange chromatography using as eluant a cationic buffer in the pH range of 7–8 and followed by the same buffer containing sodium chloride. A suitable cationic buffer in this pH range is for example Tris HCl. The fraction eluted with the NaCl-containing buffer is collected, concentrated and further purified by gel filtration chromatography using the same cationic buffer. Fractions are collected and assayed for the presence of active component. A convenient initial system for monitoring the eluate is to assay against *Bacillus subtilis*. Those fractions showing inhibition zones are pooled, concentrated and further purified by anionic-exchange chromatography using as initial eluant a cationic buffer having pH in the range of 7–8 and continues with a linear gradient of increasing ionic strength. Active fractions are checked for homogeneity by sodium dodecyl-sulfatepolyacrylamide gel electrophoresis (SDS-PAGE), isoelectric focusing, and HPLC techniques. Fractions judged to be homogeneous are pooled and lyophilized to yield the active protein.

Antibiotic

Kedarcidin is a potent protein antitumor antibiotic composed of a single chain polypeptide and a nonprotein chromophore. Although samples of the antibiotic submitted for physico-chemical characterization and biological testings had been judged to be homogeneous by SDS-PAGE, isoelectric focusing, and HPLC, during the sequencing experiments, it was discovered that the antibiotic was comprised of one major variant and one or two minor variants. The variants differ in the initial N-terminal amino acid sequence of the polypeptide as will be described later. The separation or isolation of the individual variants is not required for antitumor activity.

The present inventions also encompasses variants of kedarcidin wherein the peptide portion of the antibiotic :nay be altered by techniques known in the art to produce fragments and derivatives thereof, e.g. by deletion, addition or substitution of certain amino acids along the primary structure of the peptide, without substantially altering the antitumor activity of the antibiotic as described herein.

Amino Acid Composition

Using standard methods well known in the art, the amino acid composition of the purified protein was determined and is listed in Table VI.

TABLE VI

| | Amino acid composition of kedarcidin | | | | |
|---|---|---|---|---|---|
| | Yield | | Residues | | |
| | nmol | mol % | (a) | (b) | |
| asp | 2.765 | 8.1 | 10.1 | 9.3 | (6) |
| asn | | | | | (3) |
| thr | 3.18 | 9.3 | 11.6 | 10.6 | (11) |
| ser | 3.163 | 9.3 | 11.5 | 10.6 | (12) |
| glu | | | | | (4) |
| gln | 1.928 | 5.7 | 7.0 | 6.5 | (2) |
| pro | 1.615 | 4.7 | 5.9 | 5.4 | (4) |
| gly | 5.529 | 16.2 | 20.1 | 18.5 | (18) |
| ala | 5.566 | 16.3 | 20.3 | 18.6 | (18) |
| val | 3.731 | 11 | 13.6 | 12.5 | (13) |
| met | 0.2873 | 0.8 | 1.1 | 1.0 | (1) |
| ile | 0.8531 | 2.5 | 3.1 | 2.9 | (3) |
| leu | 1.298 | 3.8 | 4.7 | 4.3 | (4) |
| tyr | 0.6274 | 1.8 | 2.3 | 2.1 | (2) |
| phe | 1.565 | 4.6 | 5.7 | 5.2 | (5) |
| his | 0.6235 | 1.8 | 2.3 | 2.1 | (1) |
| lys | 0.3196 | 0.9 | 1.2 | 1.1 | (0) |
| arg | 1.001 | 2.9 | 3.7 | 3.3 | (3) |
| cys | 0 | 0 | 0 | 0 | (4) |
| trp | 0 | 0 | 0 | 0 | (0) |

(a) Number of residues per peptide by assuming a molecular weight of 12,000 for the peptide.
(b) Number of residues per peptide by assuming a total of 114 residues. Values in parenthesis indicate the number of residues per peptide determined by amino acid sequence analysis

Amino Acid Sequence

For amino terminal sequence analysis, Kedarcidin was reduced with 2-mercaptoethanol and further purified by SDS-PAGE (15% acrylamide) and recovered from the gels by electroelution or electroblotting.

For most enzymatic cleavages Kedarcidin was used without further purification. Kedarcidin was reduced with 20 mM dithiothreitol in 100 μl of 0.4M Tris-HCl buffer, pH 8.5, containing 6M guanidine HCl, 0.1% $Na_2$ EDTA, for 2 h at 50° C., and subsequently S-pyridylethylated with 100 mM 4-vinylpyridine, overnight at RT. The reaction was stopped by adding 10 μl of 2-mercaptoethanol, for 1 h at 50° C. The reagents were removed by dialysis against 5% (v/v) acetic acid for 24 h, and the modified Kedarcidin subsequently dried in a Speedvac centrifugal concentrator (Savant Instruments).

Enzymatic cleavage of S-pyridylethylated Kedarcidin by ASP-N enzyme or *S. aureus* V8 protease was done in 40 μl of 01.M Tris-acetic acid buffer, pH 8.0, containing 0.7M urea, at 37° C. overnight using enzyme/substrate ratio of 1:100 (ASP-N) or 1:10 (V8 protease). Trypsin digestion was done in 40 μl of 0.1M Tris-acetic acid buffer, pH 8.0, at 37° C. overnight at an enzyme/substrate ratio of 1 to 20. The enzymatic digests were acidified with trifluoroacetic acid (TFA) to pH 2.0 and separated by reversed phase HPLC.

Peptide purification by rpHPLC was performed on a Model 130 A separation system (Applied Biosystems, Inc.) and carried out at 40° C. on an RP-300 column (2.1×100 mm; Applied Biosystems, Inc.). Linear acetonitrile gradients composed of 0.1% TFA in water as starting buffer and 60% acetonitrile containing 0.085% TFA as limiting buffer were employed for elution. Peptides were collected manually. Amino acid sequence determinations were performed on an automated amino acid sequencer (Model 475 A, Applied Biosystems, Inc.) using standard techniques.

The major variant polypeptide consists of 114 amino acid residues. The amino acid sequence is determined to be as follows:

N-terminus
H—ala—ser—ala—ala—val—ser—val—ser—pro—ala—thr—gly—
leu—ala—asp—gly—ala—thr—val—thr—val—ser—ala—ser—
gly—phe—ala—thr—ser—thr—ser—ala—thr—ala—leu—gln—
cys—ala—ile—leu—ala—asp—gly—arg—gly—ala—cys—asn—
val—ala—glu—phe—his—asp—phe—ser—leu—ser—gly—gly—
glu—gly—thr—thr—ser—val—val—val—arg—arg—ser—phe—
thr—gly—tyr—val—met—pro—asp—gly—pro—glu—val—gly—
ala—val—asp—cys—asp—thr—ala—pro—gly—gly—cys—gln—
ile—val—val—gly—gly—asn—thr—gly—glu—tyr—gly—asn—
ala—ala—ile—ser—phe—gly—OH.
C-terminus Two minor variants have been identified; one lacks the first alanine of the major variant, and the second lacks the first two amino acids, i.e. alanine and serine of the major variant.

Molecular Weight Determination (a) by gel filtration/HPLC method.

Using a TSK-G2000 SW column (7.5×300 mm) (LKB Produkter AB, Sweden) gel filtration is performed using 50mM Tris HCl buffer containing 0.5M NaCl (pH 7.4) at a flow rate of 0.5 ml/ml. Alternatively, a Waters Associates Protein Analysis Column I-125 may be used with 0.2M Tris acetate as eluant at a flow rate of 1 ml/min. The molecular weight is estimated to be 17,000 daltons from the reference curve obtained from standard molecular weight markers (Bio Rad Laboratories).

(b) Sodium dodecyl sulfate - polyacrylamide gel electrophoresis method.

A sample of the protein and molecular weight markers (purchased from Diversified Biotech, Me.) are mixed with an equal volume of Seprasol (ready-to-use protein solubilization liquid containing sucrose and a tracking dye) and heated for 3 minutes at 90° C. immediately before electrophoresis. Electrophoresis is run at 300V in Seprabuff (Tris-glycine-SDS, pH 8.3) until the tracking dye reached the bottom of the gel. The gel is then immersed in a staining solution (1.25g Comassie BB R-250, 92 ml glacial acetic acid in 908 ml of aqueous methanol) for at least 10 hours, then immersed in a destaining solution (75 ml acetic acid and 50 ml of methanol in 875 ml of water) until the background of the gel becomes transparent. Seprasol and seprebuff were purchased from Integrated Separation System, Massachusetts. The molecular weight is estimated to be 12,400 daltons by this method.

Isoelectric Focusing

The gel used for focusing is prepared by mixing

| | |
|---|---|
| 29.1% acrylamide in water | 10 ml |
| 0.9% N,N'-methylene-bis-acrylamide in water | 10 ml |
| glycerin | 7 ml |
| 1802 Ampholine pH 2.5-4 | 3 ml |
| water | q.s. to 60 ml |

The resultant solution is degassed for 10 minutes and 1.5 ml of 1% ammonium persulfate in water and 10 μl of N,N,N',N'-tetramethylethylenediamine are added thereto. The mixture is poured into the casting mold and allowed to polymerize. The electrode solutions used are 1M phosphoric acid at the anode and 2% 1809 Ampholine pH 6–8 at the cathode. The focusing experiment is performed at 25 watt constant power for 2 hours. The percentage refers to percent weight in volume. Th ®isoelectric point is determined to be 3.65 and the migration distance from the cathode is 6.25 cm.

Biological Activity

The antitumor activity of the protein was evaluated against transplantable murine P388 leukemia. $CDF_1$ mice were implanted intraperitoneally (ip) or intravenously (iv) with $10^6$ P388 leukemia cells obtained from DBA/2 donor mice bearing this transplantable murine leukemia. Against ip-implanted P388 leukemia, the mice were treated ip with either saline (control mice) or doses of kedarcidin once daily for five consecutive days beginning one day post-tumor inoculation. Against iv-implanted P388 leukemia, the mice received kedarcidin iv on Days 1, 3 and 5 post-implant. These animals were observed daily and their deaths recorded. Average body weight changes (from the day of leukemia implant to the day of last treatment) were determined for all groups as a means of reflecting drug toxicity. The incidence of mice alive in each group on Day 5 post-tumor implant was recorded as an additional means of assessing drug toxicity. No therapeutic result was considered as meaningful if more than one mouse per treatment group had died by Day 5. Treatment groups consisted of either 4 or 6 mice; control groups contained 10 mice. The number of mice, if any, surviving to Day 30 (the last day of the experiments) was also recorded. At the end of the experiment the median survival time (MST) for each group was determined and used to calculate the % T/C which is the ratio of the MST of a treated group and the MST of the control group multiplied by 100. A % T/C value of 125 or greater indicates significant antitumor activity. The in vivo data are presented in Tables IV and V.

TABLE IV

Antitumor activity against ip implanted P388 leukemia.

| Lot | Dose[a] Dil. or mg/kg/inj | Med. surv. time (d) | % T/C | Av. wt. change (g) | No. of mice alive on d5 |
|---|---|---|---|---|---|
| D16F411 | Dil. 1–40 | 7.0 | 74 | −1.9 | 4/4 |
| | Dil. 1–80 | 10.0 | 105 | −1.2 | 4/4 |
| | Dil. 1–160 | 12.5 | 132 | −1.0 | 4/4 |
| | Dil. 1–320 | 18.5 | 195 | −1.9 | 4/4 |
| | Control | 9.5 | — | 0.2 | 10/10 |
| D18F413 | 0.27 | 7.0 | 70 | −1.9 | 4/6 |
| | 0.09 | 15.0 | 150 | −0.8 | 6/6 |
| | 0.03 | 17.0 | 170 | −1.7 | 6/6 |
| | 0.01 | 15.0 | 150 | −0.3 | 6/6 |
| D18G414[b] | 0.09 | 9.5 | 95 | −1.3 | 6/6 |
| | 0.03 | 15.5 | 155 | −1.2 | 6/6 |
| | 0.01 | 14.5 | 145 | −0.5 | 6/6 |
| | 0.0033 | 14.0 | 140 | −0.2 | 6/6 |
| Control | | 10.0 | — | 0 | 10/10 |

[a]drug administered ip once daily for 5 consecutive days beginning one day post tumor inoculation.
[b]lyophilized and reconstituted preparation of the same sample represented by lot D18F413.

TABLE V

Antitumor activity against ip implanted P388 leukemia.

| Lot | Dose[a] dil. or mg/kg/inj | Med. surv. time (d) | % T/C | Av. wt. change (g) | No. of mice alive on d5 |
|---|---|---|---|---|---|
| D18F413 | 0.32 | 6.0 | 75 | −3.1 | 6/6 |
|  | 0.16 | 7.5 | 94 | −3.2 | 6/6 |
|  | 0.08 | 11.0 | 138 | −1.4 | 6/6 |
|  | 0.04 | 12.5 | 156 | −0.6 | 6/6 |
|  | 0.02 | 10.0 | 125 | 0.1 | 6/6 |
|  | 0.01 | 8.0 | 100 | 1.2 | 6/6 |
| D16F411 | Dil. 1-25 | 7.0 | 88 | −2.9 | 6/6 |
|  | Dil. 1-50 | 10.5 | 131 | −1.6 | 6/6 |
|  | Dil. 1-100 | 13.0 | 163 | −1.2 | 6/6 |
|  | Dil. 1-200 | 9.5 | 119 | −0.2 | 6/6 |
|  | Dil. 1-400 | 9.0 | 113 | 0.5 | 6/6 |
|  | Dil. 1-800 | 8.0 | 100 | 0.8 | 6/6 |
|  | Control | 8.0 | — | — | 10/10 |

[a]drug administered iv on day 1,3, and 5 post-tumor implant.

Kedarcidin was also evaluated against murine B16 melanoma implanted intraperitoneally with 0.5 ml of 10% tumor brei. Ten mice were used for each dose level. The drug was administered intraperitoneally once daily for nine consecutive days beginning one day after tumor implantation. The numbers of mice alive on day 10 and at the end of the experiment, i.e., day 60 were recorded. The test results are presented in Table VI. % T/C values of 125 or greater indicate significant antitumor activity.

TABLE VI

Antitumor activity of kedarcidin against ip implanted B16 melanoma

| Dose (mg/kg/dose) | MST (d) | % T/C | Av. wt. change (g) | No. of mice alive on d5 (60)* |
|---|---|---|---|---|
| 0.256 | 16.0 | 97 | −2.7 | 9/10 |
| 0.128 | 24.5 | 148 | −1.3 | 10/10 |
| 0.064 | 26.5 | 161 | 0.3 | 10/10 |
| 0.032 | 31.5 | 191 | 1.0 | 10/10 |
| 0.016 | 32.5 | 197 | 0.6 | 10/10 |
| 0.008 | 34.0 | 206 | 0.6 | 9/10 |
| 0.004 | 27.0 | 164 | 0.3 | 10/10(1) |
| 0.002 | 21.5 | 130 | 0 | 10/10 |
| Control | 16.5 | — | 1.3 |  |

*Number in parenthesis = number of mice alive on day 60 post tumor implant.

The test results given in Tablves IV, V and VI demonstrate that antibiotic kedarcidin is a potent material displaying reproducible in vivo antitumor activity against murine leukemia P388 and B16 melanoma. The activity observed was manifested by increases in life-span against ip implanted B16 melanoma, and both ip as well as iv implanted P388, the latter representing a more difficult form of the disease to treat effectively because of its disseminated nature. Kedarcidin has also been evaluated against subcutaneously implanted B16 melanoma, M5076 murine lung tumor, and intracranially implanted P388 leukemia but did not show significant activity in these animal models.

The invention includes within its scope pharmaceutical compositions containing an effective tumor-inhibiting amount of the antibiotic of the present invention in combination with an inert pharmaceutically acceptable carrier or diluent. Such compositions may also contain other active antitumor agents and may be made up in any pharmaceutical form appropriate for the desired route of administration. Examples of such compositions include solid compositions for oral administration such as tablets, capsules, pills, powders and granules, liquid compositions for oral administration such as solutions, suspensions, syrups or elixirs and preparations for parenteral administration such as sterile solutions, suspensions or emulsions. They may also be manufactured in the form of sterile solid compositions which can be dissolved in sterile water, physiological saline or some other sterile injectable medium immediately before use.

For use as an antitumor agent, optimal dosages and regiments for a given mammalian host can be readily ascertained by those skilled in the art. It will, of course, be appreciated that the actual dose used will vary according to the particular composition formulated, the route of administration and the particular situs, host and disease being treated. Many factors that modify the action of the drug will be taken into account including age, weight, sex, diet, time of administration, route of administration, rate of excretion, condition of the patient, drug combinations, reaction sensitivities and severity of the disease.

The present invention is illustrated by the following examples which are not intended to be construed as limiting the scope of the invention.

EXAMPLE 1

Preparation of vegetative culture of Streptoalloteichus Strain L585-6.

Streptoalloteichus sp. Strain L585-6 (ATCC 53650) was maintained and transferred in test tubes on slants of yeast-malt extract agar which consists of

| dextrose | 4.0 g |
|---|---|
| yeast extract | 4.0 g |
| malt extract | 10.0 g |
| CaCO$_3$ | 1.5 g |
| agar | 15 g |
| distilled water | q.s. 1 liter |

With each transfer the agar slant was incubated at 28° C. for two weeks. Vegetative culture was prepared by transferring the surface growth from the slant culture to a 500 ml Erlenmeyer flask containing 100 ml of a sterile medium consisting of

| cerelose (Corn Products) | 30 g |
|---|---|
| Pharmamedia (Traders Oil Mill Co.) | 10 g |
| Nutrisoy (Archer Daniels Midland Co.) | 10 g |
| CaCO$_3$ | 3 g |
| distilled water | q.s. to 1 liter |

This vegetative culture was incubated at 28° C. for 72 hours on a rotary shaker set at 250 rev/min.

EXAMPLE 2

Fermentation in shake flasks.

Five mls of the vegetative culture of Example 1 was inoculated into 500 ml Erlenmeyer flasks each containing 100 ml of a production medium consisting of

| glycerol | 30 g |
|---|---|
| Pharmamedia | 10 g |
| Distiller's solubles (Nutrition Product Co.) | 15 g |
| fish meal (Menhaden) | 10 g |
| CaCO$_3$ | 6 g |
| distilled water | q.s. to 1 liter |

The production culture was incubated at 28° C. on a rotary shaker set at 250 rev/min. Production of the protein antibiotic was monitored with microbial assay using B. subtilis and in vitro cytotoxicity assays using murine melanoma cell line B16-F10 and human tumor cell lines. Optimal production was generally reached at 144 to 168 hours.

EXAMPLE 3

Fermentation in tanks.

Twenty-five mls of the vegetative culture of Example 1 was inoculated into a 2 l Vitro bottle containing 500 ml of the same vegetative medium. The second stage seed culture was further incubated at 28° C. for 72 hours on a rotary shaker with the agitation rate set at 250 rev/min. 500 ml of the second stage seed culture were inoculated into a New Brunswick Microgen fermentor (16 liters nominal volume) containing 10 liters of production medium having the composition given in Example 2. The fermentation was carried out at 28° C., aeration of one volume per minute and the agitation set at 250 rev/min. The production of antibiotic kedarcidin was monitored with the appropriate in vitro bioassays.

EXAMPLE 4

Isolation and purification of kedarcidin.

10 L of raw fermentation broth was mixed with 6 l of Dicalite and the resulting thin slurry was filtered on a Dicalite pad. The insolubles were discarded and the filtrate was pumped through a Zeta Prep 250 QAE ion-exchange cartridge (LKB-Produkter AB, Sweden) at a rate of 30 ml/min. The cartridge had been previously equilibrated with 2 l of 50 mM Tris-HCl buffer, pH 7.4. The effluent was collected. The cartridge was washed with 1 L of 50mM Tris-HCl buffer, pH 7.4 and then eluted with 500 ml of 50 mM Tris-HCl buffer, pH 7.4 containing 0.5 mole of NaCl. The eluate was collected and concentrated from 500 ml to 100 ml using an Amicon standard ultrafiltration cell fitted with an Amicon YM5 membrane. The concentrated solution was percolated into a gel filtration column (5×100 cm) packed with 1400 ml of Ultrogel AcA54 (LKB-Produkter AB, Sweden) in an equal volume of 50 mM Tris-HCl buffer. The Ultrogel bed had been equilibrated with 5 L of 50 mM Tris-HCl buffer, pH 7.4. The charged column was eluted with 2 L of 50 mM Tris-HCl buffer, pH 7.4 at 60 ml/ml. After an initial aliquot of 450 ml, 10 ml fractions were collected and each fraction was assayed against *B. subtilis*. Those fractions giving inhibition zones (fractions 83–133) were pooled and then concentrated to 100 ml by ultrafiltration. The concentrated solution was percolated into the ion exchange column (2.5×15 cm) packed with a slurry of 70 ml of DEAE Trisacryl (LKB-Produkter AB, Sweden) in an equal volume of 50 mM Tris-HCl buffer. The Trisacryl bed had been equilibrated with 10 column volumes of 50 mM Tris-HCl buffer. The charged column was initially eluted with 10 column volumes of 50 mM Tris-HCl buffer, followed by a 300 ml linear gradient (slope=0.1M/hr) of 100% 50 mM Tris-HCl buffer to 100% of 50 mM Tris-HCl buffer containing 0.5M NaCl at a flow rate of 60 ml/hr. A total of 47 5-ml fractions were collected and assayed against *B. subtilis*. Active fractions 25–37 were pooled and subjected to analytical gel filtration/HPLC using Waters Protein Analysis column I-125, 0.2M Tris acetate, pH 7.0 at a flow rate of 1 ml/min as eluant, and UV detector at 260 nm. Under these conditions, the chromatogram shows a single peak at retention time of 8.3 minutes. The pooled fractions were also judged to be homogenous by isoelectric focusing and SDS-PAGE using conditions previously described. The concentration of the active component was estimated to be 4.25 mg/ml by lyophilization of a 10 ml aliquot and correcting for buffer weight.

What is claimed is:

1. Antibiotic kedarcidin characterized as follows:
   (a) appearance: buff-colored solid;
   (b) molecular weight: 12,400 daltons by SDS-polyacrylamide gel electrophoresis method; 17,000 by gel filtration/HPLC method;
   (c) UV spectrum: substantially as shown in FIG. 1 having absorption peaks at 1204, 258 and 306 nm;
   (d) isoelectric point: 3.65; and
   (e) having a non-protein chromophore and a polypeptide having an amino acid sequence as follows:
   X-ala-ala-val-ser-val-ser-pro-ala-thr-gly-leu-ala-asp-gly-ala-thr-val-thr-val-ser-ala-ser-gly-phe-ala-thr-ser-thr-ser-ala-thr-ala-leu-gln-cys-ala-ile-leu-ala-asp-gly-arg-gly-ala-cys-asn-val-ala-glu-phe-his-asp-phe-ser-leu-ser-gly-gly-glu-gly-thr-thr-ser-val-val-val-arg-arg-ser-phe-thr-gly-tyr-val-met-pro-asp-gly-pro-glu-val-gly-ala-val-asp-cys-asp-thr-ala-pro-gly-gly-cys-gln-ile-val-val-gly-gly-asn-thr-gly-glu-tyr-gly-asn-ala-ala-ile-ser-phe-gly-OH;
   wherein
   X is selected from the group consisting of H-ala-ser, H-ser, and H.

2. A pharmaceutical composition which comprises a tumor-inhibiting amount of kedarcidin and a pharmaceutically acceptable carrier.

* * * * *